US00PP07847P

United States Patent [19]

VandenBerg

[11] Patent Number: Plant 7,847

[45] Date of Patent: Mar. 31, 1992

[54] CHRYSANTHEMUM PLANT NAMED 'ANNA'

[75] Inventor: Cornelis P. VandenBerg, Salinas, Calif.

[73] Assignee: Yoder Brothers, Inc., Barberton, Ohio

[21] Appl. No.: 565,710

[22] Filed: Aug. 13, 1990

[51] Int. Cl.[5] ..... A01H 5/00

[52] U.S. Cl. ..... Plt./74

[58] Field of Search ..... Plt./74, 82.2

[56] References Cited

PUBLICATIONS

Sunnyslope Gardens 1987, Chrysanthemum Catalog, pp. 12, 29–30. San Gabriel, Calif.

Sunnyslope Gardens 1982 Chrysanthemum catalog. p. 20, San Gabriel, Calif.

Kings Mums 1989 Catalog, Clements, Calif., p. 22.

*Primary Examiner*—Howard J. Locker

*Attorney, Agent, or Firm*—Foley & Lardner

[57] ABSTRACT

A Chrysanthemum plant named Anna particularly characterized by its flat capitulum form; spooned daisy capitulum type; yellow ray floret color; diameter across face of capitulum of 57 to 76 mm when fully opened; spreading and prolific branching pattern, with 7 to 9 breaks after pinch when grown outside under natural daylength in fall flowerings, and 6 to 7 breaks after pinch when grown in 10 cm pots for spring flowerings; natural season flowering date of August 25 when planting rooted cuttings June 23 in Salinas, Calif., and September 29 to October 1 when planting rooted cuttings June 15 to June 18 in Hightstown, N.J.; flowering response of 49 to 53 days after rooting in no light/no shade programs in spring; plant height of 30 to 36 cm when grown in fall under natural daylength with no growth regulators, and of 20 cm when grown in 10 cm pots in spring with 1 to 2 applications of 2500 ppm B-9 SP; and durable, uniform performance.

3 Drawing Sheets

The present invention comprises a new and distinct cultivar of Chrysanthemum, botanically known as *Dendranthema grandiflora*, and referred to by the cultivar name Anna.

Anna, identified as 87-345001, was originated from a cross made by Cornelis P. VandenBerg in a controlled breeding program in Salinas, Calif., in 1985.

The female parent of Anna was an unnamed seedling, identified as 79-M56002, and described as a dark yellow quilled decorative garden mum having a flower diameter of 64 mm, a natural season flower date of August 20 to 28 in Salinas, Calif., and of September 10 to 20 in Hightstown, N.J., a flowering response in spring of 46 to 50 days, and a plant height of 18 to 25 cm in fall natural season flowerings, and of 20 to 23 cm in spring flowerings in 10 cm pots with no growth regulator. The female parent of Anna was discarded from the breeding program in October 1986 because of its early crown budding and uneven performance because of this trait.

The male parent of Anna was the cultivar Allure, disclosed in U.S. Plant Pat. No. 5,989 from which a detailed description can be obtained. A description of the important phenotypical characteristics of Allure can be found in attached Chart A, comparing certain characteristics of Anna with the same characteristics of Allure.

The stated cross was made with the objective to expand the range of quilled decorative garden mums, and the obtaining of a spooned daisy out of this cross was completely unexpected. In addition, the natural season flowering response in New Jersey of Anna is considerably slower than the response of either parent, and Anna has a taller plant height in natural season fall flowerings than either parent.

The first act of asexual reproduction of Anna was accomplished when vegetative cuttings were taken from the initial selection in December 1987 in a controlled environment is Salinas, Calif., by technicians working under the supervision of Cornelis P. VandenBerg.

Horticultural examination of controlled flowerings of successive plantings has shown that the unique combination of characteristics as herein disclosed for Anna are firmly fixed and are retained through successive generations of asexual reproduction.

Anna has not been observed under all possible environmental conditions. The phenotype may vary significantly with variations in environment such as temperature, light intensity and daylength.

The following observations, measurements and comparisons describe plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Anna, which, in combination, distinguish this Chrysanthemum as a new and distinct cultivar:

1. Flat capitulum form.
2. Spooned daisy capitulum type.
3. Yellow ray floret color.
4. Diameter across face of capitulum of 57 to 76 mm. when fully opened.
5. Branching pattern is spreading and prolific, with 7 to 9 breaks after pinch when grown outside under natural daylength in fall flowerings, and 6 to 7 breaks after pinch when grown in 10 cm pots for spring flowerings.
6. Natural season flower date of August 25 when planting rooted cuttings on June 23 in Salinas, Calif., and of September 29 to October 1 when planting rooted cuttings June 15 to June 18 in Hightstown, N.J.

7. Flowering response of 49 to 53 days after rooting in no light/no shade programs in spring.

8. Plant height of 30 to 36 cm when grown in fall under natural daylength with no growth regulators, and of 20 cm when grown in 10 cm pots in spring with 1 to 2 applications of 2500 ppm B-9 SP.

9. Durable, uniform performance.

The accompanying photographic drawings show typical inflorescence and leaf characteristics of Anna, with the colors being as nearly true as possible with illustrations of this type.

Sheet 1 is a color photograph of Anna grown as a pinched spray pot mum with 4 cuttings in a 15 cm. pot.

Sheet 2 is a black and white photograph of three views of the inflorescence of Anna.

Sheet 3 is a black and white photograph showing the upper and under sides of the leaves of Anna at 3 stages of development (mature, intermediate and immature).

Sheets 2 and 3 include a measuring tape in centimeters, thereby illustrating the dimensions of the flower and leaves.

Of the commercial cultivars known to the inventor, the most similar in comparison to Anna is the male parent Allure. Reference is made to attached Chart A, which compares certain characteristics of Anna to the same characteristics of Allure.

Similar traits are ray floret color, branching pattern, and flowering response in spring. Only one natural season flowering in fall was conducted in Salinas. Anna has a spooned daisy flower type, while Allure has a daisy flower type. Anna has a larger flower diameter, a more spreading branching pattern, a slower natural season flowering response in New Jersey, and a taller plant height in natural season flowerings when compared with Allure.

Since filing the application resulting in the plant patent for Allure, more detailed information from different locations has been collected for Allure, which information is presented in Chart A.

In the following description color references are made to The Royal Horticultural Society Colour Chart. The color values were determined on plant material grown as a pinched spray pot mum in Salinas, Calif. on May 30, 1990.

Classification:

*Botanical.*—*Dendranthema grandiflora* cv Anna.

*Commercial.*—Flat spooned daisy spray pot mum and garden mum.

Inflorescence

A. Capitulum:

*Form.*—Flat.

*Type.*—Spooned daisy.

*Diameter across face.*—57 to 76 mm when fully opened.

B. Corolla of ray florets:

*Color (general tonality from a distance of three meters).*—Yellow.

*Color.*—Upper surface: 5A. Under surface: 5B.

*Shape.*—Spooned, with uneven spoonlengths, with the majority of the spoons being 80 to 90% of the total length of the petal. Petals are straight, ribbed.

C. Corolla of disc florets:

*Color (mature).*—7A.

*Color (immature).*—3A, overlaid with 144B.

D. Reproductive organs:

*Androecium.*—Present on disc florets only; moderate pollen.

*Gynoecium.*—Present on both ray and disc florets.

Plant

A. General appearance:

*Height.*13 30 to 36 cm when grown in fall under natural daylength with no growth regulators, and 20 cm when grown in 10 cm pots in spring with 1 to 2 applications of 2500 ppm B-9 SP.

*Branching pattern.*—Spreading and prolific, with 7 to 9 breaks after pinch when grown outside under natural daylength in fall flowerings, and 6 to 7 breaks after pinch when grown in 10 cm pots for spring flowerings.

B. Foliage:

*Color (upper surface).*—147A.

*Color (under surface).*—147B.

*Shape.*—See photograph. Foliage is relatively large for a garden mum.

CHART A

| CULTIVAR | ANNA | ALLURE |
|---|---|---|
| Ray floret color | Yellow | Yellow |
| Capitulum form and type | Flat spooned daisy | Flat daisy |
| Diameter across face of capitulum | 57 to 76 mm | 51 to 70 mm |
| Branching pattern | Spreading and prolific | Semi-spreading |
| Breaks fall outdoors | 7 to 9 | 6 to 8 |
| Breaks in 10 cm pots | 6 to 7 | 5 to 8 |
| Nat. season flower date: | | |
| in Salinas, CA | Aug 25 | Aug 21 to 26 |
| in Hightstown, NJ | Sep 29 to Oct 1 | Sep 21 to 27 |
| Plant height: | | |
| in natural season fall | 30 to 36 cm | 23 to 33 cm |
| in 10 cm pots spring | 20 cm (with B-9) | 18 to 25 cm |

COMPARISONS MADE OF PLANTS GROWN AS UNDER NATURAL SEASON OUTDOOR CONDITIONS IN SALINAS, CALIFORNIA AND IN HIGHSTOWN, NEW JERSEY AND IN SPRING FLOWERING PROGRAMS IN SALINAS, CALIFORNIA

I claim:

1. A new and distinct Chrysanthemum plant named Anna, as described and illustrated.

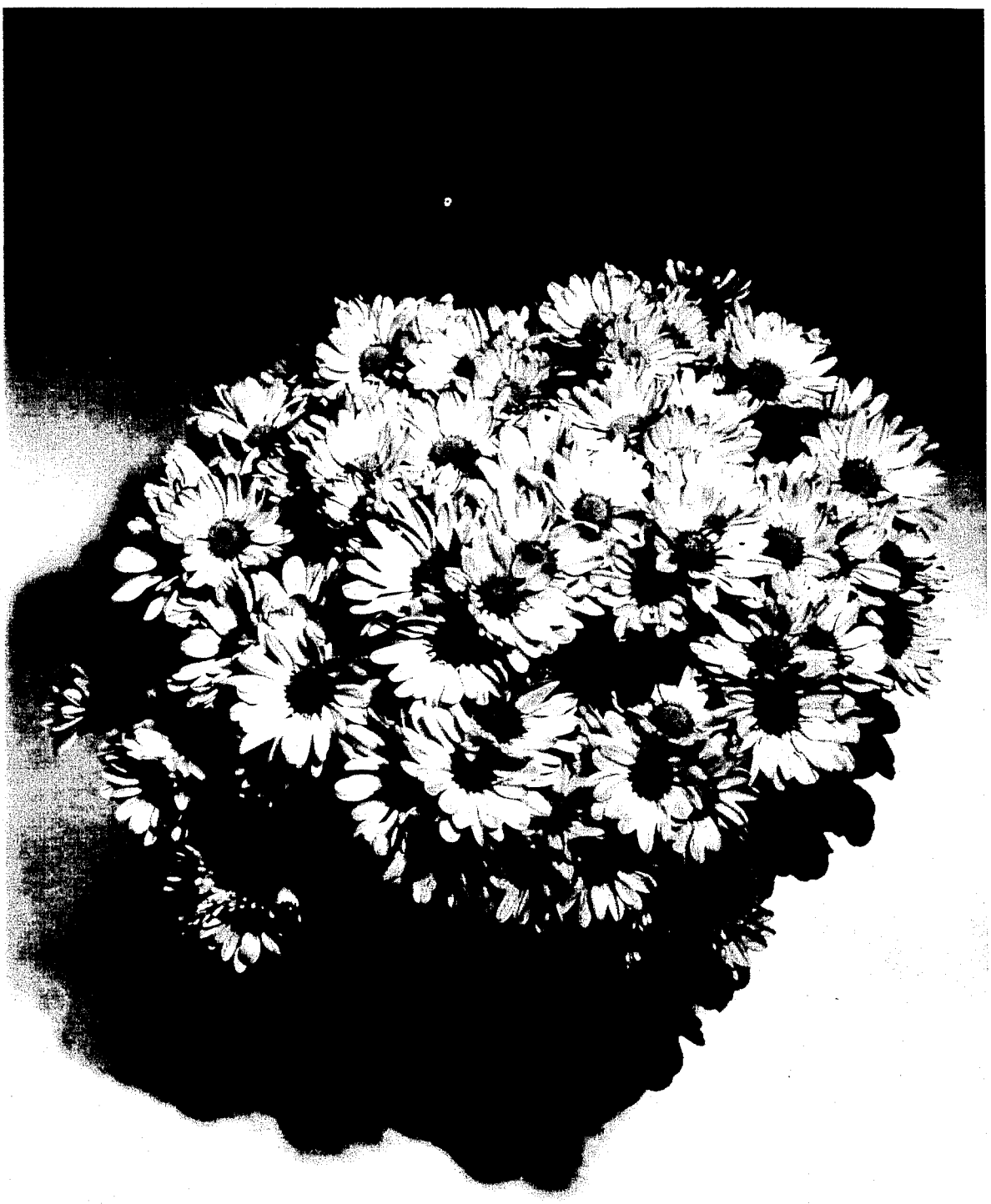

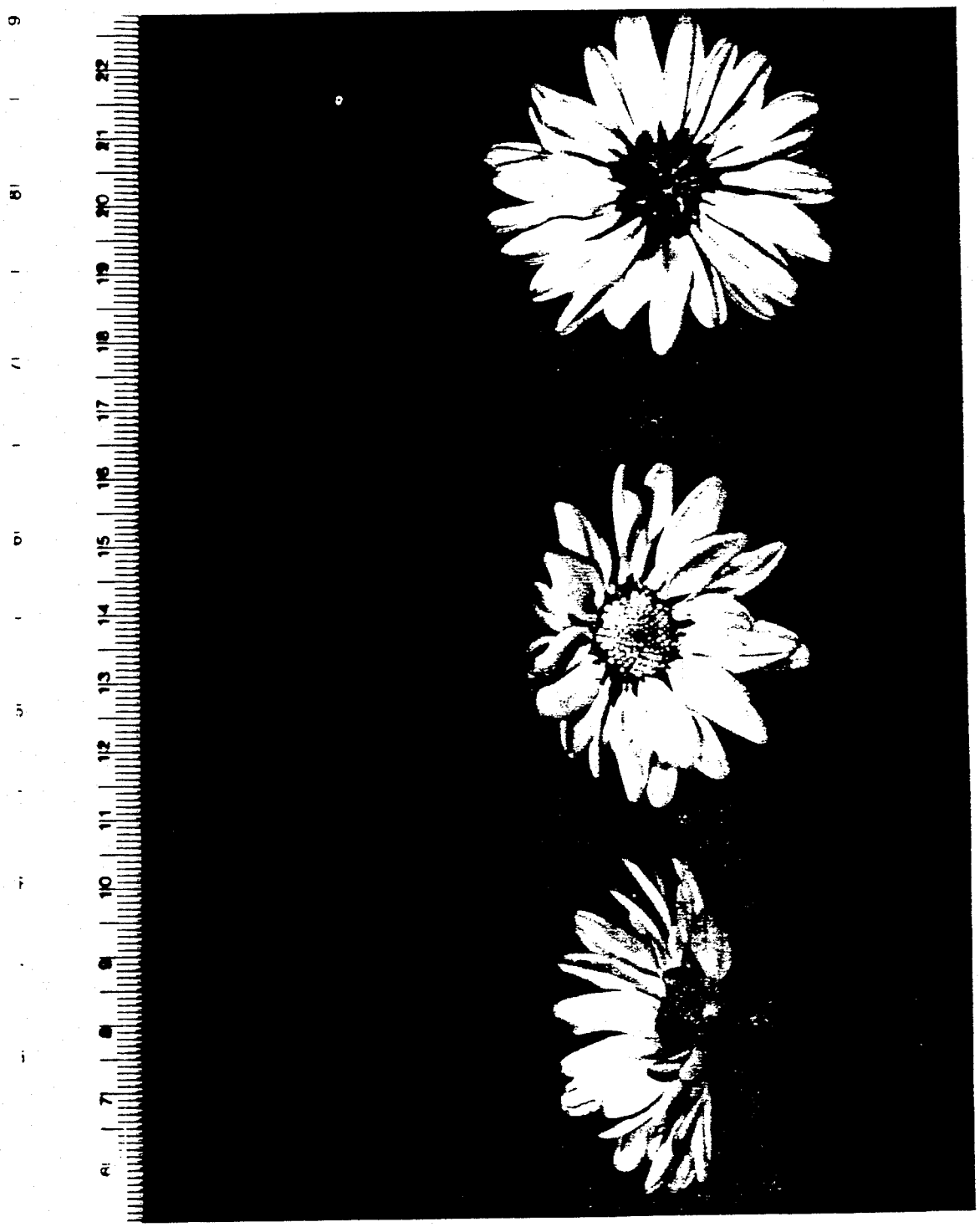

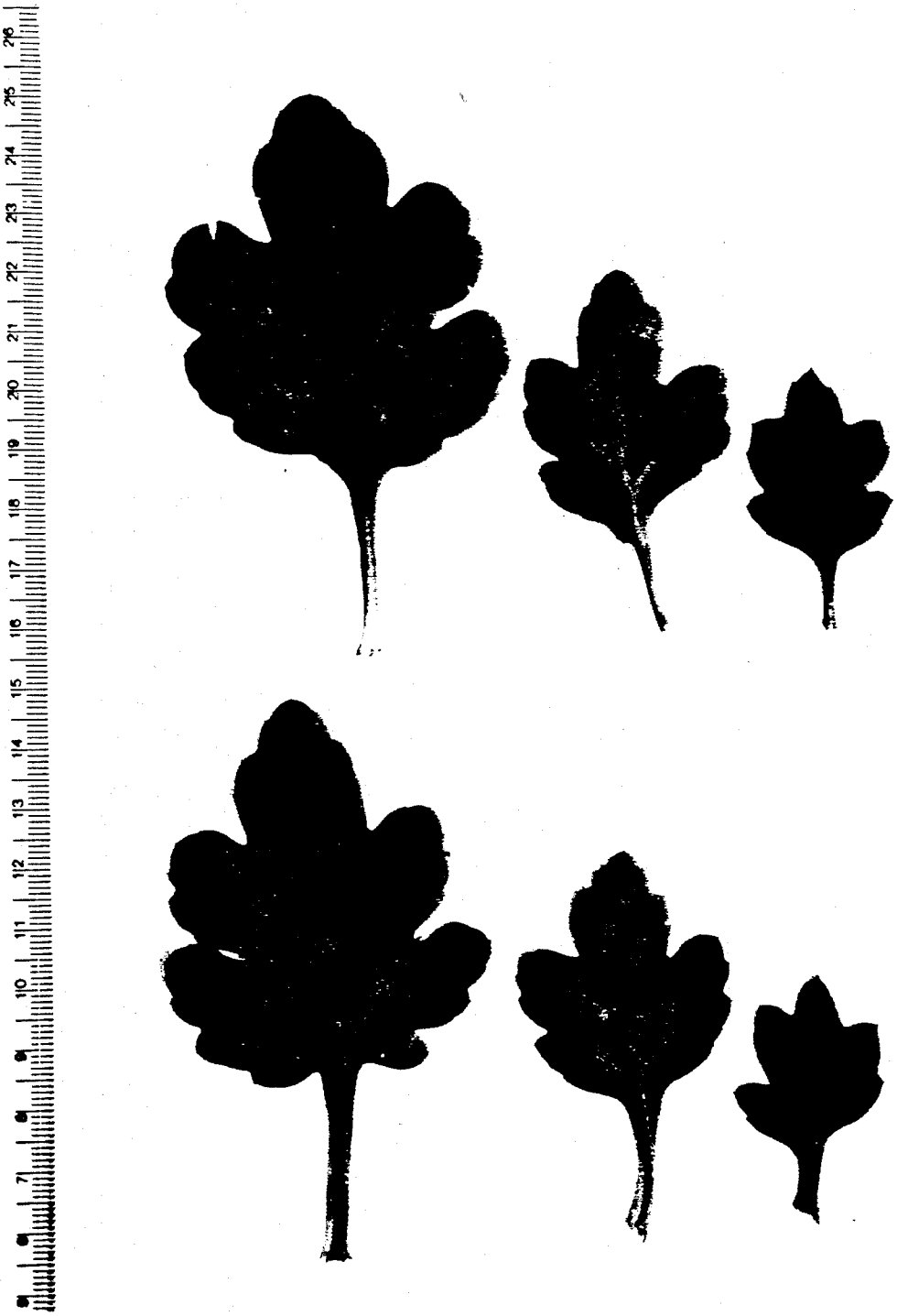

* * * * *